United States Patent [19]

Fischer et al.

[11] 4,188,344

[45] Feb. 12, 1980

[54] PRODUCTION OF 4-(M,M'-DITERT.-BUTYL-P-HYDROXY-PHENYL)-BUTAN-2-ONES

[75] Inventors: Roman Fischer, Mutterstadt; Werner Fliege, Otterstadt; Wolfgang Koernig, Mannheim; Bernd Meissner, Heidelberg, all of Fed. Rep. of Germany

[73] Assignee: BASF Aktiengesellschaft, Fed. Rep. of Germany

[21] Appl. No.: 866,382

[22] Filed: Jan. 3, 1978

Related U.S. Application Data

[63] Continuation of Ser. No. 443,826, Feb. 19, 1974, abandoned.

[30] Foreign Application Priority Data

Feb. 24, 1973 [DE] Fed. Rep. of Germany ....... 2309370

[51] Int. Cl.$^2$ .............................................. C07C 45/00
[52] U.S. Cl. ................................................. 260/590 E
[58] Field of Search ........................ 260/590 R, 590 E

[56] References Cited

U.S. PATENT DOCUMENTS

| | | | |
|---|---|---|---|
| 2,435,087 | 1/1948 | Luten et al. | 260/621 |
| 2,975,216 | 3/1961 | Spacht | 260/624 |
| 3,098,874 | 7/1963 | Porsch | 260/590 R |
| 3,226,443 | 12/1965 | Meier et al. | 260/590 R |
| 3,859,311 | 1/1975 | Symon et al. | 260/590 R |

FOREIGN PATENT DOCUMENTS

| | | | |
|---|---|---|---|
| 2145308 | 3/1973 | Fed. Rep. of Germany | 260/590 |
| 392548 | 7/1958 | Switzerland | 260/590 |

*Primary Examiner*—James H. Reamer
*Attorney, Agent, or Firm*—Keil & Witherspoon

[57] ABSTRACT

4-(m,m'-ditert.-butyl-p-hydroxyphenyl)-butan-2-ones are produced by reaction of a 4-hydroxybutanone-(2) with 2,6-ditert.-butylphenol in the presence of a strong acid at elevated temperature. The compounds obtainable by the process, particularly 4-(m,m'-ditert.-butyl-p-hydroxyphenyl)-butane-2-one, are starting materials for the production of dyes, pest control agents and plastics auxiliaries and particularly of stabilizers for polyolefins and polyamides.

6 Claims, No Drawings

PRODUCTION OF 4-(M,M'-DITERT.-BUTYL-P-HYDROXYPHENYL)-BUTAN-2-ONES

This is a continuation, of application Ser. No. 443,826 filed Feb. 19, 1974 now abandoned.

The invention relates to a process for the production of 4-(m,m'-ditert.-butyl-p-hydroxyphenyl)-butan-2-ones by reaction of a 4-hydroxybutanone-(2) with 2,6-ditert.-butylphenol in the presence of a strong acid at elevated temperature.

It is known from German Printed Application (DAS) No. 1,192,206 that 4-(3',5'-ditert.-butyl-4'-hydroxyphenyl)-butan-2-one can be prepared by reaction of 2,6-ditert.-butylphenol with methyl vinyl ketone in the presence of metallic potassium and tert.-butanol. It is a disadvantage of this method that uneconomical catalysts are used and the procedure is troublesome and unsatisfactory as regards reliability, yield, and purity of the end product, particularly in commercial operation.

It is an object of the present invention to provide a new process for producing 4-(m,m'-ditert.-butyl-p-hydroxyphenyl)-butan-2-ones in better yields and purity, particularly on a commercial scale, in a simpler, more economical and more reliable manner.

We have found that a 4-(m,m'-ditert.-butyl-p-hydroxyphenyl)-butan-2-one of the formula (I):

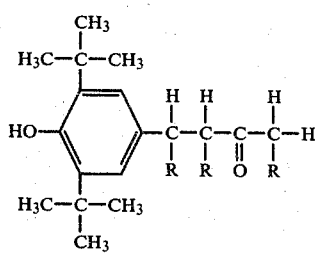

in which the individual radicals R may be identical or different and each is hydrogen or an aliphatic radical is obtained advantageously by reacting 2,6-ditert.-butylphenol with a 4-hydroxybutanone-(2) of the formula (II):

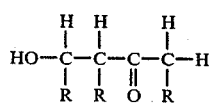

in which R has the above meanings, in the presence of a strong acid at elevated temperature.

When 4-hydroxybutan-2-one is used the reaction may be represented by the following equation:

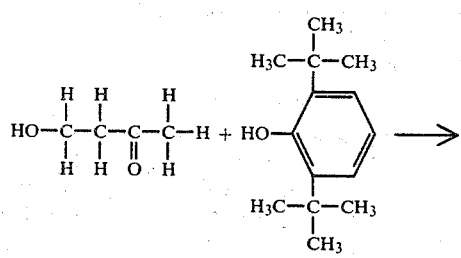

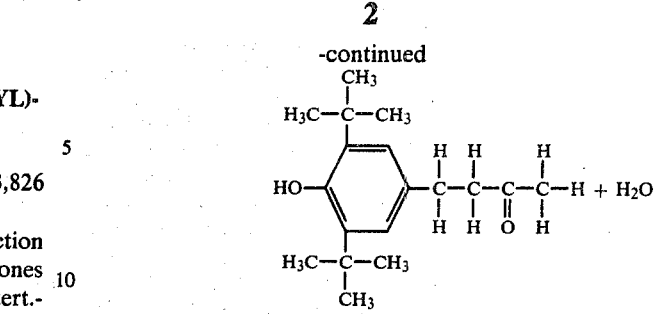

The process according to the invention surprisingly gives 4-(m,m'-ditert.-butyl-p-hydroxyphenyl)-butane-2-ones in a better yield and purity, particularly on a commercial scale, in a simpler, more economical and more reliable manner than the prior art methods.

The starting material: 2,6-ditert.-butylphenol may also be used as the technical grade product, for example down to a content of at least 95% by weight of 2,6-ditert.-butylphenol. 4-hydroxybutan-2-one may be prepared in a simple and economical manner, for example by reaction of acetone with formaldehyde by the method disclosed in German Printed Application (DAS) No. 1,277,235.

It is not necessary to use pure starting material (II), for example 4-hydroxybutan-2-one. If desired a technical product may be used which generally contains from 80 to 94% by weight of 4-hydroxybutan-2-one as well as for example mesityl oxide and small amounts of water. A starting material (II), for example 4-hydroxybutan-2-one, having a purity of at least 90% by weight is preferred. 2,6-ditert.-butylphenol may be reacted with the starting material (II) in a stoichiometric amount or in excess, preferably in a ratio of from 0.7 to 3 moles of 2,6-ditert.-butylphenol to 1 mole of starting material (II). Preferred starting materials (II) and consequently preferred end products (I) are those in whose formulae the individual radicals R are identical or different and each is alkyl of one to four carbon atoms or particularly hydrogen. The said radicals may bear as substituents groups which are inert under the reaction conditions, for example alkyl groups or alkoxy groups in each case of one to three carbon atoms, or nitro groups. A particularly advantageous starting material (II) for the process is 4-hydroxybutan-2-one and consequently 4-(m,m'-ditert.-butyl-p-hydroxyphenyl)-butan-2-one is a particularly advantageous end product (I). Examples of other starting materials (II) are: 4-methyl-4-hydroxybutan-2-one, 3-ethyl-4-hydroxybutan-2-one, 1-ethyl-4-hydroxybutan-2-one, 1,4-dimethyl-4-hydroxybutan-2-one and 1,3,4-trimethyl-4-hydroxybutan-2-one.

The reaction is carried out as a rule at a temperature of from 30° to 160° C., advantageously from 50° to 100° C. and preferably from 81° to 100° C., at atmospheric or superatmospheric pressure, continuously or batchwise. An organic solvent which is inert under the reaction conditions may be used such as an alkanol, particularly of one to four carbon atoms, for example ethanol, methanol, isopropanol or isobutanol, an ether such as di-n-propyl ether, tetrahydrofuran or dioxane; or mixtures of the same. Advantageous amounts of solvent are from 50 to 90% by weight based on starting material (II).

Strong acids in the present context are organic or inorganic acids which are inert under the reaction conditions and which have an acid exponent (pKs) of from −7 to +2.16. Ullmanns Encyklopadie der technischen Chemie, volume 15, page 2 may be referred to for a definition of acid exponents or pKs values. Examples of suitable acids are concentrated sulfuric acid, advantageously of from 90 to 98% by weight strength, phosphoric acid, conveniently of from 85 to 90% by weight strength. Hydrogen chloride gas, perchloric acid, boric acid, sulfonic acids such as benzenesulfonic acid and p-toluenesulfonic acid, trichloroacetic acid, and acid ion exchangers such as those described in Houben-Weyl, "Methoden der Organischen Chemie", volume I/1, pages 528 et seq., preferably polystyrenesulfonic acid resins, phenolsulfonic acid resind and polyfluoroethylenesulfonic acids may also be used. The preferred acid is concentrated sulfuric acid, particularly of the said concentration. The acid is conveniently used in an amount of from 0.15 to 0.5 and preferably from 0.2 to 0.3 part by weight per part by weight of starting material (II).

When using hydrogen chloride gas, a sulfonic acid or an ion exchanger as catalyst it is necessary also to use a solvent. When hydrogen chloride gas is used the process is conveniently carried out by dissolving the 2,6-ditert.-butylphenol in the solvent, saturating this solution with hydrogen chloride gas and allowing the starting material (II) to flow in under the abovementioned conditions while further passing in a weak current of hydrogen chloride.

The reaction may be carried out as follows: A mixture of 2,6-ditert.-butylphenol, starting material (II), acid and solvent (if any) is held for from two to twenty hours and preferably from four to ten hours at the reaction temperature. In carrying out the process the 2,6-ditert.-butylphenol is conveniently mixed with the strong acid and optionally with a solvent and the starting material (II) with or without solvent is allowed to flow into this mixture in the course of from one hour to fourteen hours and preferably from two to ten hours, with intense mixing for example by stirring, shaking or with the use of a vibromixer. The reaction mixture is then allowed to react further for another one hour to six hours and preferably from two to four hours with intense mixing. The end product is isolated from the reaction mixture by a conventional method, for example by neutralization of the reaction mixture, for example with an alkali metal hydroxide, separation of the salt formed or if necessary the organic phase from the aqueous phase, and fractionation of the organic phase. Any solvent and unreacted 2,6-ditert.-butyl phenol recovered in the distillation is reused.

Compounds which can be prepared according to the process of the invention, and particularly 4-(m,m'-ditert.-butyl-p-hydroxyphenyl)-butan-2-one, are valuable starting materials for the production of dyes, pesticides and plastics auxiliaries, particularly stabilizers for polyolefins and polyamides. For example 4-(m-m'-ditert.-butyl-p-hydroxyphenyl)-butan-2-ol may be prepared by reduction of 4-(m,m'-ditert.-butyl-p-hydroxyphenyl)-butan-2-one under pressure with Raney cobalt or Raney nickel at elevated temperature, for example by the process described in German OLS 2.309,375. 4-(3,5-ditert.-butyl-4-hydroxyphenyl)-2-aminobutane is similarly obtained by reductive amination of 4-(3,5-ditert.-butyl-4-hydroxyphenyl)-butane-2-one by a conventional method with Raney nickel as catalyst, for example by the process described in OLS 2,309,377. Both substances are stabilizers for polyolefins and polyamides and starting materials for the production of such stabilizers. The end products according to the invention and particularly 4-(m,m'-ditert.-butyl-p-hydroxyphenyl)-butan-2-one are also suitable as antioxidants, aging retardants and stabilizers for substances which are destroyed, discolored or embrittled by the action of heat, light, oxygen or ozone; examples of such substances are lubricating oils, fuel oils and other oils of mineral, vegetable or animal origin, waxes, soaps, fats, gasolines, natural and synthetic rubber, natural resins and plastics such as polyethylene and polypropylene. The end products (I) in the form of their melts are special solvents for alkylphenols, for example 2,6-diethylphenol, 2,6-dimethylphenol, 2,4-dimethylphenol, and perfumes or components for perfumes having odor notes similar to those of bilberries, raspberries and blackberries. The abovementioned publications may be referred to as regards uses.

The following Examples illustrate the invention. The parts specified in the Examples are parts by weight.

EXAMPLE 1

1030 parts of 2,6-ditert.-butylphenol and 150 parts of concentrated sulfuric acid (96% by weight) are heated in 600 parts of ethanol to 85° C. while stirring. 520 parts of 95% by weight 4-hydroxybutan-2-one is added within nine hours. The reaction mixture is then stirred for another two hours at 85° C., cooled to ambient temperature and neutralized with caustic soda solution. After the aqueous phase and the sodium sulfate have been removed the mixture is processed by distillation. 717 parts of 2,6-ditert.-butylphenol is recovered. 368 parts of 4-(m,m'-ditert.-butyl-p-hydroxyphenyl)-butan-2-one having a melting point of 45.5° C. to 47° C. is obtained. This is a yield of 88% of theory based on reacted 2,6-ditert.-butylphenol.

EXAMPLE 2

1030 parts of 2,6-ditert.-butylphenol and 150 parts of concentrated sulfuric acid (95% by weight) are heated to 75° C. in 400 parts of ethanol while stirring. 196 parts of 95% by weight of 4-hydroxybutan-2-one is added within two hours. The reaction mixture is then stirred for another three hours at 75° C. The mixture is worked up analogously to Example 1. 691 parts of 2,6-ditert.-butylphenol is recovered. 316 parts of 4-(m,m'-ditert.-butyl-p-hydroxyphenyl)-butan-2-one having a melting point of 46° to 47° C. is obtained; this is a yield of 70% of theory based on reacted 2,6-ditert.-butylphenol.

EXAMPLE 3

1030 parts of 2,6-ditert.-butylphenol and 100 parts of p-toluenesulfonic acid are heated to 85° C. in 600 parts of ethanol while stirring. 520 parts of 95% by weight 4-hydroxybutan-2-one is added within eight hours. The reaction mixture is then stirred for another two hours at 85° C., allowed to cool to ambient temperature and neutralized with caustic soda solution. After the aqueous phase has been separated the mixture is worked up by distillation. 742 parts of 2,6-ditert.-butylphenol is recovered. 330 parts of 4-(m,m'-ditert.-butyl-p-hydroxyphenyl)-butan-2-one having a melting point of 46° to 47° C. is obtained; this is a yield of 86% of theory based on reacted 2,6-ditert.-butylphenol.

EXAMPLE 4

2060 parts of 2,6-ditert.-butylphenol and 200 parts of concentrated sulfuric acid (95% by weight) is heated to 85° C. in 1200 parts of ethanol while stirring. 1040 parts of 95% by weight 4-hydroxybutan-2-one is added within nine hours. The reaction mixture is then stirred for another three hours at 85° C. The mixture is worked up analogously to Example 1. 927 parts of 2,6-ditert.-butylphenol is recovered. 1208 parts of 4-(m,m'-ditert.-butyl-p-hydroxyphenyl)-butan-2-one having a melting point of 46° to 47° C. is obtained; this is a yield of 80% of theory based on the reacted 2,6-ditert.-butylphenol.

We claim.

1. A process for the production of a 4-(m,m'-ditert.-butyl-p-hydroxyphenyl)-butan-2-one of the formula (I):

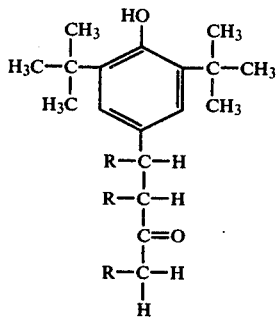

in which the individual radicals R may be identical or different and each is hydrogen, an alkyl radical of 1–4 carbon atoms or the said alkyl bearing as substituents alkyl groups or alkoxy groups in each case of 1–3 carbon atoms, or nitro groups wherein 2,6-ditert.-butylphenol is reacted with a 4-hydroxybutanone-(2) of the formula (II):

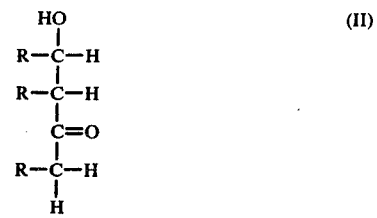

in which R has the meanings given above, in the presence of acid having an acid exponent (pKs) of from −7 to +2.16 at an elevated temperature of from 30° to 160° C.

2. A process as claimed in claim 1 wherein 4-hydroxybutan-2-one is used as starting material.

3. A process as claimed in claim 1 wherein the reaction is carried out with a ratio of from 0.7 to 3 moles of 2,6-ditert.-butylphenol per mole of starting material (II).

4. A process as claimed in claim 1 wherein the reaction is carried out at a temperature of from 81° to 100° C.

5. A process as claimed in claim 1 wherein the reaction is carried out in the presence of an organic solvent which is inert under the reaction conditions.

6. A process as claimed in claim 1 wherein the reaction is carried out in the presence of sulfuric acid, phosphoric acid, hydrogen chloride gas, perchloric acid, boric acid, a sulfonic acid, trichloroacetic acid or an acid ion exchanger.

* * * * *